United States Patent [19]

Asato et al.

[11] Patent Number: 4,876,272
[45] Date of Patent: Oct. 24, 1989

[54] MONO- AND DIEPOXIDE DERIVATIVES OF LL-F28249 COMPOUNDS

[75] Inventors: Goro Asato, Titusville; Susan Y. Tamura, Hamilton Sq., both of N.J.

[73] Assignee: American Cyanamid Company, Stamford, Conn.

[21] Appl. No.: 22,849

[22] Filed: Mar. 6, 1987

[51] Int. Cl.$^4$ .............................................. A61K 35/66
[52] U.S. Cl. .................................. 514/450; 549/264
[58] Field of Search ......................... 549/264; 514/450

[56] References Cited

U.S. PATENT DOCUMENTS 4,530,921 7/1985 Mrozik ................................ 549/264

FOREIGN PATENT DOCUMENTS 2166436A 5/1986 United Kingdom .

Primary Examiner—Glennon H. Hollrah
Assistant Examiner—Amelia A. Owens
Attorney, Agent, or Firm—Estelle J. Tsevdos

[57] ABSTRACT

The present invention relates to novel mono- C(26,27) and diepoxide C(14,15;26,27) derivatives of LL-F28249α, β, ε, ζ, θ and ι compounds. The LL-F28249 compounds (collectively) are isolates from the fermentation broth of Streptomyces cyaneogriseus subspecies noncyanogenus having deposit accession number NRRL-15773. The compounds of this present invention are derived by regioselective epoxidation of 5,23-0,0-bis-silylated LL-F28249 compounds at low temperature, followed by desilylation. These novel compounds have anthelmintic, insecticidal, ectoparasiticidal, nematicidal and acaricidal activity and also are useful intermediates for the preparation of further biologically active compounds. Compositions containing these described derivatives as active ingredients thereof are described.

9 Claims, No Drawings

MONO- AND DIEPOXIDE DERIVATIVES OF LL-F28249 COMPOUNDS

BACKGROUND OF THE INVENTION

The present invention relates to new mono and diepoxide derivatives of the compounds collectively defined as LL-F28249. These LL-F28249 antibiotics preferably are produced by the fermentation of the microorganism *Streptomyces cvaneooriseus* subspecies *noncyanogenus*, deposited in the NRRL under deposit accession No. 15773. The morphological characteristics of this culture, compounds and method for their production are disclosed in European Patent Application No. 170,006, incorporated herein by reference.

The LL-F28249 components are complex macrolids which have 5 olefinic bonds. The regioselective epoxidation of the C(26,27)-olefinic bond concomitant with or without epoxidation at the C(14,15)-olefinic bond is the subject matter of the instant application. These mono- and diepoxide derivatives possess anthelmintic, ectoparasitic, insecticidal, acaricidal and nematicidal activity and, therefore, are useful in the prevention, control or treatment of infections in warm-blooded animals, as well as infestations of agricultural crops.

SUMMARY OF THE INVENTION

The present invention provides novel C(26,27)-epoxide and C(14,15; 26,27)-diepoxide derivatives of the compounds designated LL-F28249α, β, ε, ζ, θ and ι.

These LL-F28249 compounds have the following structural formula:

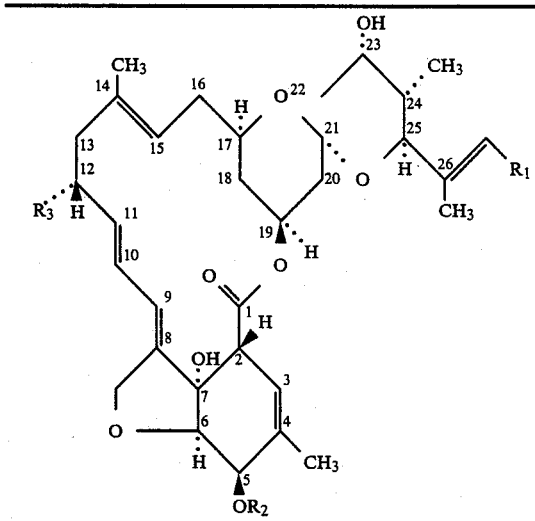

| Component | $R_1$ | $R_2$ | $R_3$ | $R_4$ |
|---|---|---|---|---|
| LL-F28249α | $CH(CH_3)_2$ | H | $CH_3$ | $CH_3$ |
| LL-F28249β | $CH_3$ | H | $CH_3$ | $CH_3$ |
| LL-F28249ε | $CH(CH_3)_2$ | H | H | $CH_3$ |
| LL-F28249ζ | $CH_2CH_3$ | H | $CH_3$ | $CH_3$ |
| LL-F28249θ | $CH(CH_3)_2$ | H | $CH_3$ | $CH_2CH_3$ |
| LL-F28249ι | $CH(CH_3)_2$ | H | $CH_2CH_3$ | $CH_3$ |

The compounds of the present invention are useful anthelmintics, ectoparasiticides, insecticides, acaricides and nematicides in treating preventing or controlling such diseases in warm-blooded animals, such as poultry, cattle, sheep, swine, rabbits, horses, dogs, cats and human beings and agricultural crops.

Although these diseases have been recognized for years and therapies exist for the treatment and prevention of the diseases, the present invention provides novel compounds in the search for effective such therapy. For instance, U.S. Application for Letters Patent Ser. Nos. 907,283, 907,188, 907,281, 907,259, 907,187 and 907,284 of Asato and Asato et al, filed on Sept. 12, 1986 and incorporated herein by references thereof provide compounds for such treatments. Also U.S. Application for Letters Patent Ser. Nos. 022,850, 022,906, 022,848, 022,846 and 022,847, filed of Asato et al filed concurrently herewith and incorporated herein by reference thereof provide compounds for such treatments.

U.S. Pat. No. 3,950,360, Aoki et al, Apr. 13, 1976 discloses certain antibiotic substances obtained by culturing microorganism, said compounds being useful as insecticides and acaricides. Further, an entire series of U.S. patents relates to certain compounds produced by the fermentation of *Streptomyces avermitilis* (U.S. Pat. Nos. 4,171,314, Chabala et al, Oct. 16, 1979; 4,199,569, Chabala et al, Apr. 22, 1980; 4,206,205, Mrozik et al, June 3, 1980; 4,310,519, Albers-Schonberg, Jan. 12, 1982; 4,333,925, Buhs et al, June 8, 1982). 4,423,209, Mrozik, Dec. 27, 1983 relates to the process of converting some of these less desirable components to more preferred ones. Finally, British Patent Application No. 2166436 A discloses antibiotics also, as does Belgium Patent Application No. 904,709A.

The present compounds or the pharmaceutically and pharmacologically acceptable salts thereof exhibit excellent and effective treatment, prevention and/or control of these serious diseases of warm-blooded animals.

It is an object of the present invention, therefore, to provide novel C(26,27)-epoxide and C(14,15; 26,27)-diepoxide derivatives of LL-F28249α, β, ε, ζ, θ and ι. It is a further object to provide a process for the preparation of these derivatives and to provide methods for preventing, treating or controlling endo- and ectoparasitic (collectively parasitic) insect, nematode and acarid infections and infestations in warm-blooded animals and agricultural crops by providing compositions containing prophylactically, therapeutically, pharmaceutically or pesticidally effective amounts of the present compound. A further object of these compounds is as intermediates for the preparation of other novel antiparasitic and insecticidal compounds.

These and other objects of the invention will become apparent by the more detailed description of the invention provided hereinbelow.

DETAILED DESCRIPTION OF THE INVENTION

The LL-F28249 compounds which may act as precursors of the present compounds are represented by the following structural formula,

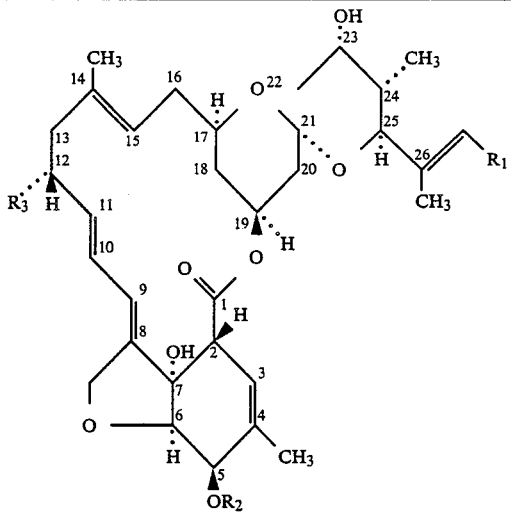

| Component | R₁ | R₂ | R₃ | R₄ |
|---|---|---|---|---|
| LL-F28249α | CH(CH₃)₂ | H | CH₃ | CH₃ |
| LL-F28249β | CH₃ | H | CH₃ | CH₃ |
| LL-F28249ε | CH(CH₃)₂ | H | H | CH₃ |
| LL-F28249ζ | CH₂CH₃ | H | CH₃ | CH₃ |
| LL-F28249θ | CH(CH₃)₂ | H | CH₃ | CH₂CH₃ |
| LL-F28249ι | CH(CH₃)₂ | H | CH₂CH₃ | CH₃ |

The compounds of the present invention are represented by the following structural formula,

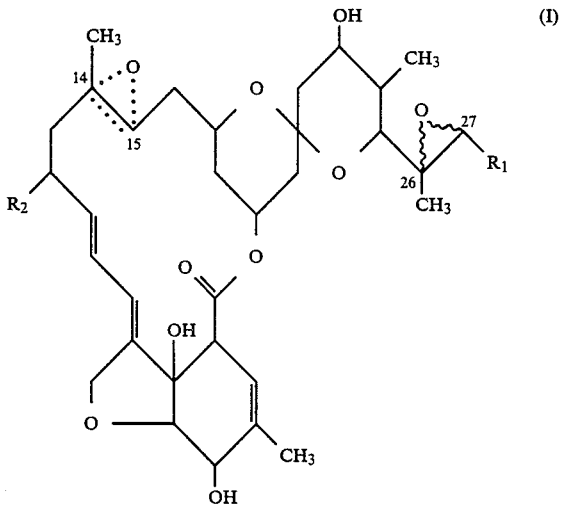

(I)

wherein $R_1$ is methyl or isopropyl; $R_2$ is hydrogen, methyl or ethyl; and the dotted triangular figure with oxygen at C(14,15) indicates that either a double bond or an epoxide is present.

Preferably, $R_1$ is isopropyl; $R_2$ is methyl; and the dotted triangular figure with oxygen at C(14,15) indicates that either a double bond or an epoxide is present.

The most preferred compound is $R_1$ as isopropyl; $R_2$ as methyl; and the dotted triangular figure with oxygen indicating a double bond.

In addition to the 23-hydroxy, further substitutions, such as ethers and esters at position 23, are readily synthesized and included within the scope of the present invention.

The monoepoxide and diepoxide compounds of the present invention are prepared by treating the appropriately-protected LL-F28249 compound with an oxidizing agent at temperature less than −15° C. The oxidant useful in the present invention is capable of selectively oxidizing the C(26,27) double bond, as well as the C(14,15) double bond, but will leave other double bonds in the molecule intact. Selectivity also is attained by controlling the temperature of the oxidation in an inert solvent, such as methylene chloride, chloroform and the like. Peroxide oxidizing agents, such as m-chloroperoxybenzoic acid, are representative of the preferred oxidants in preparing the monoepoxy and diepoxy compounds of the present invention.

Generally, a slight excess of the oxidizing agent is employed, such as 5%-20% excess, when it is desired to prepare the C(26,27) epoxide in good yield. When epoxidation at C(14,15) double bond also is desired, equivalent to a slight excess of 2 moles is . employed. These epoxides are readily separated by standard chromatographic techniques, such as column or preparative-plate chromatography.

The epoxidation also is generally conducted at temperatures less than −20° C. to −78° C. and is complete in 3-6 hours. Separation of the monoepoxide from the diepoxide is readily achieved by standard chromatographic techniques, such as column or preparative-plate chromatography.

The starting materials for the compounds of the present invention are the above-mentioned LL-F28249 fermentation products. These compounds are initially derivatized at the 5- and 23-hydroxy groups with a trisubstituted alkyl silyl group. A preferred protecting group is t-butyldimethylsilyl group. The reaction is carried out by allowing the LL-F28249 compound to react with two molar equivalents of a substituted silyl halide, preferably a silyl chloride, in an aprotic solvent such as dimethylformamide or ethylene dichloride in the presence of imidazole and/or 4-dimethylaminopyridine. The reaction is completed in 2-8 hours at 50° C. to 80° C.

The silyl groups are removed after epoxidation by stirring the silyl derivative in methanol containing an acid, such as o-toluenesulfonic acid monohydrate or acetic acid without methanol. The reaction is complete in 1-8 hours at 0° C. to 25° C., preferably at 10° C. to 25° C. It also is especially beneficial if this reaction is conducted in the presence of catalytic amount of FeCl₃.

The novel compounds of the present invention possess significant parasitical activity as anthelmintics, ectoparasiticides, insecticides, nematicides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dichtyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesphagostomum, primarily attack the intestinal tract while others, such as Haemonchus and Ostertagia, are most prevalent in the stomach, while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofiliara in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae such as Hypoderma sp., in cattle, Gastrophilus in horses, and Cuterebra sp., in rodents.

The compounds of the present invention also are useful in treating, preventing or controlling parasites which infect human beings, as well. The most common genera of parasites of the gastrointestinal tract of man are Ancylostoma, Necator, Ascaris, Strongyloides, Trichinella, Capillaria, Trichuris and Enterobius. Other medically important genera of parasites which are found in the blood or other tissues and organs outside the gastrointestinal tract are the filiarial worms such as Wuchereria, Brugia, Onchocerca and Loa, Bracunculus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola sp., carpet beetle, Attagenus sp., and the housefly Musca domestica.

Insect pests of stored grains such as Tribolium sp., Tenebrio sp., and of agricultural plants such as spider mites (Tetranychus sp.), southern army worms, tobacco budworms, boll weevils, aphids Acyrthiosiphon sp.), migratory orthopterans such as locusts and immature stages of insects living on plant tissue are controlled by the present compounds, as well as control of soil nematodes and plant parasites such as Meloidogyne sp., which may be of importance in agriculture.

The compounds of the present invention may be administered orally or parenterally for animal and human usage, while they may be formulated in liquid or solid form for agricultural use. Oral administration may take the form of a unit dose form such as a capsule, bolus or tablet, or as a liquid drench when used as an anthelmintic in mammals.

The animal drench is normally a solution, suspension or dispersion of the active ingredient, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1%, by weight. Capsules and boluses comprise the active ingredient admixed with a carrier vehicle such as starch, talc, magnesium stearate or di-calcium phosphate.

Where it is desired to administer the present derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the active present compound depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the present invention may be administered to animals parenterally, for example, by intraruminal, intramuscular, intratracheal or subcutaneous injection. In such event, the active compound is dissolved or dispersed in a liquid carrier vehicle.

For parenteral administration, the active compound is suitably admixed with an acceptable vehicle, preferably of the vegetable oil variety such as peanut oil, cotton seed oil and the like. Other parenteral vehicles such as organic preparations using solketal, propylene glycol, glycerol formal, and aqueous parenteral formulations also are used. The active compound or compounds of the present invention are dissolved or suspended in the parenteral formulation for administration. Such formulations generally contain about 0.005% to 5%, by weight of the active compound.

Although the compounds of the present invention are primarily used in the treatment, prevention or control of helminthiasis, they also are useful in the prevention and treatment of diseases caused by other parasites. For example, arthropod parasites such as ticks, lice, fleas, mites and other biting insects in domesticated animals and poultry are controlled by the present invention. These compounds also are effective in treatment of parasitic diseases that occur in other animals including human beings. The optimum amount to be employed for best results will, of course, depend upon the particular compound employed, the species of animal to be treated and the type and severity of parasitic infection or infestation. Generally, the amount useful in oral administration of these novel compounds is about 0.001 mg per kg to 10 mg per kg of animal body weight, such total dose being given at one time or in divided doses over a relatively short period of time such as 1-5 days. The preferred compounds of the invention give excellent control of such parasites in animals by administering about 0.025 mg to 5 mg per kg of body weight in a single dose. Repeat treatments are given as required to combat reinfections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active compound is present in relatively large amounts, wherein said feed premixes or supplements are suitable for direct feeding to the animal or for addition to the feed either directly or after and intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing about 0.005% to 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment and control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds also may be administered by pouring on the skin of animals via a solution. Generally, the active compounds are dissolved in suitable inert solvents, such as dimethylsulfoxide, propylene glycol or the like, alternatively in combination of solvents, for the pour-on administration.

The compounds of this invention also are useful in combating agricultural pests that inflict damage upon growing or stored crops. The present compounds are applied, using known techniques such as sprays, dusts, emulsions and the like, to the growing or stored crops to effect protection from such agricultural pests.

The present invention is illustrated by the following examples which are illustrative of said invention and not limitative thereof.

EXAMPLE 1

5,23-O,O-(Bis-tert-butyldimethylsilyl)-LL-F28249α

In 20 mL of dimethylformamide, 2.0 g of LL-F28249α, 3.72 g of t-butyldimethylsilyl chloride and 2.38 g of imidazole are heated at 60° C., in an oil bath under $N_2$, for 6 hours. The mixture is cooled, quenched with 5 mL of $H_2O$ and diluted with 100 mL of $H_2O$ and 50 mL of brine. The product is then extracted from the aqueous mixture with 2×50 mL of $Et_2$). The combined $Et_2O$ extracts are washed with 2×25 mL of $H_2O$, 10 mL of brine and dried over $MgSO_4$. Removal of $Et_2O$ affords the title compound which is identified by mass spectrometry and nuclear magnetic resonance (NMR) spectrometry.

EXAMPLES 2 AND 3

LL-F28249α-C(26,27)-Epoxide and
LL-F28249α-C(14,15;26,27)-Diepoxide

In 5 mL of $CH_2Cl_2$, 105.4 mg of 5,23-O,O-(bis-t-butyldimethylsilyl)-LL-F28249α is dissolved, and the solution is cooled in dry-ice/acetone bath while 27.8 mg of m-chloroperoxybenzoic acid in 300 mL is added. After an hour of stirring under $N_2$, the temperature is raised to −42° C. for 2 hours and −20° C. for an hour.

The solution is washed with 1 mL of saturated Na solution, 1 mL of saturated $NaHCO_3$ solution and 1 mL of brine. After drying over $Na_2SO_4$, the solution is evaporated, and the residue is chromatographed on silica gel in a flash chromatography apparatus using 5% EtOAc/hexane followed by 10% EtOAc/hexane. Fractions 16 to 20 afford 45 mg of the monoepoxide, while fractions 31-36 afford 12.1 mg of the monoepoxide.

In 1 mL of MeOH, 30.3 mg of epoxide is stirred with 10.2 mg of p-toluenesulfonic acid monohydrate for 7.5 h under $N_2$. The mixture is diluted with 1 mL of saturated $NaHCO_3$ solution and 5 mL of $H_2O$ and extracted with 3×2 mL of $Et_2O$. The combined $Et_2O$ extracts washed with brine, dried over $MgSO_4$, filtered and evaporated to dryness. The residue is chromatographed on silica gel using 2% isopropanol/$CH_2Cl_2$ on a flash chromatography apparatus to afford 9.4 mg of LL-F28249α-C(26,27)-epoxide, which is identified by mass spectrometry and NMR spectroscopy.

Similarly, the diepoxide is treated with p-toluenesulfonic acid to afford deblocked LL-F28249α-C(14,15;26,27)-diepoxide.

EXAMPLES 4–7

5,23-O,O-(Bis-tert-butyldimethylsilyl)-LL-F28249 compounds

Using the procedure of Example 1, the following bis-silylated products are prepared:

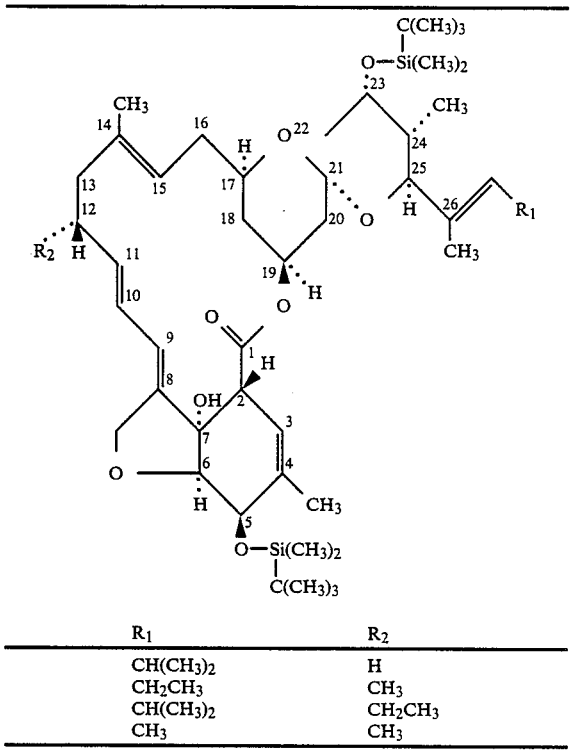

| R₁ | R₂ |
|---|---|
| CH(CH₃)₂ | H |
| CH₂CH₃ | CH₃ |
| CH(CH₃)₂ | CH₂CH₃ |
| CH₃ | CH₃ |

EXAMPLES 8–15

LL-F28249-C(26,27)-epoxides and
LL-F28249-C(14,15;26,27)-diepoxides

Using the method of Example 2, the following epoxides and diepoxides of structure (I) are prepared:

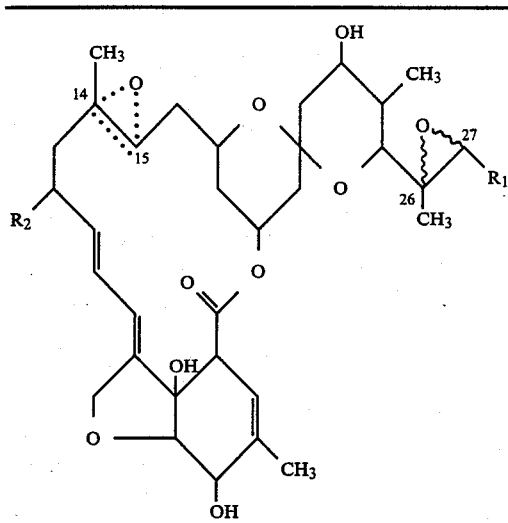

(I)

| $R_1$ | $R_2$ |
|---|---|
| $CH(CH_3)_2$ | H |
| $CH_2CH_3$ | $CH_3$ |
| $CH(CH_3)_2$ | $CH_2CH_3$ |
| $CH_3$ | $CH_3$ |

What is claimed is:

1. A compound represented by formula (I),

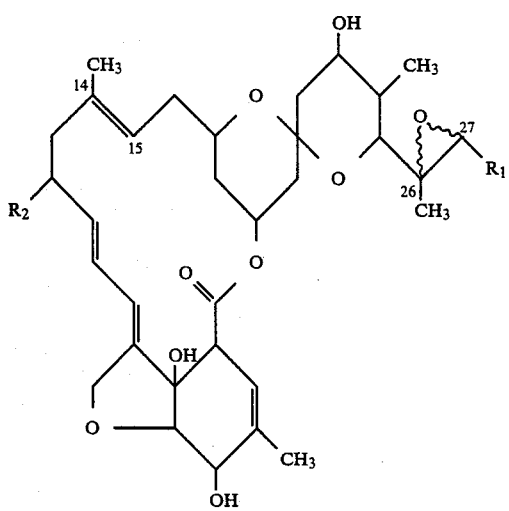

(I)

wherein $R_1$ is methyl or isopropyl; and $R_2$ is hydrogen, methyl or ethyl.

2. A compound according to claim 1, wherein $R_1$ is isopropyl; and $R_2$ is methyl.

3. A method for the prevention, treatment or control of parasitic infections in warm-blooded animals, said method comprising: orally topically or parenterally administering to an animal infected with endo- or ectoparasited, parasiticidally-effective amount of a compound represented by structural formula (I),

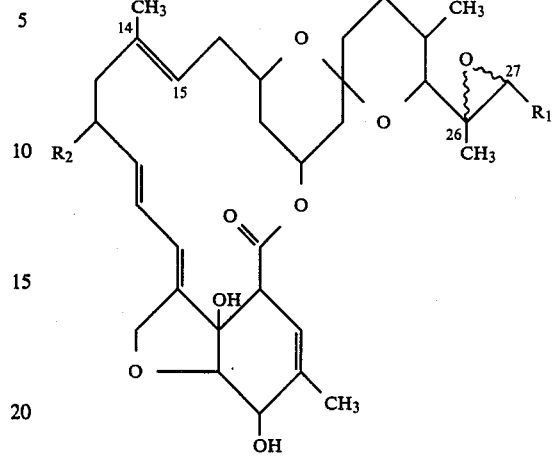

(I)

wherein $R_1$ is methyl or isopropyl; and $R_2$ is hydrogen, methyl or ethyl.

4. A method according to claim 3, wherein said compound is $R_1$ as isopropyl; and $R_2$ as methyl.

5. A method for protecting crops, trees, shrubs, stored grains and ornamentals from insects or acarids which infest them, said method comprising: applying an acaricidally or insecticidally-effective amount of a compound represented by structural formula (I),

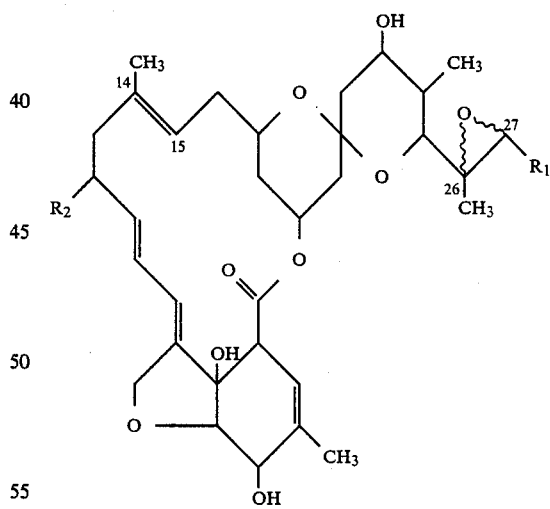

(I)

wherein $R_1$ is methyl or isopropyl; and $R_2$ is hydrogen, methyl or ethyl.

6. A method according to claim 5, wherein said compound is $R_1$ as isopropyl; and $R_2$ as methyl.

7. A method for the control of plant nematodes, said method comprising: applying to the foliage plants, the soil in which they are grown or into the trunks thereof, a nematocidally-effective amount of a compound represented by structural formula (I)

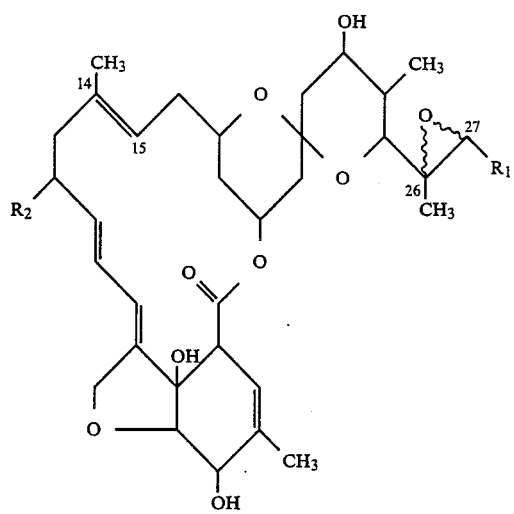

(I)

wherein $R_1$ is methyl or isopropyl; and $R_2$ is hydrogen, methyl or ethyl.

8. A method according to claim 7, wherein said compound is $R_1$ as isopropyl; and $R_2$ as methyl.

9. A composition comprising: a pharmacologically, acaricidally or insecticidally effective amount of a compound represented by structural formula (I),

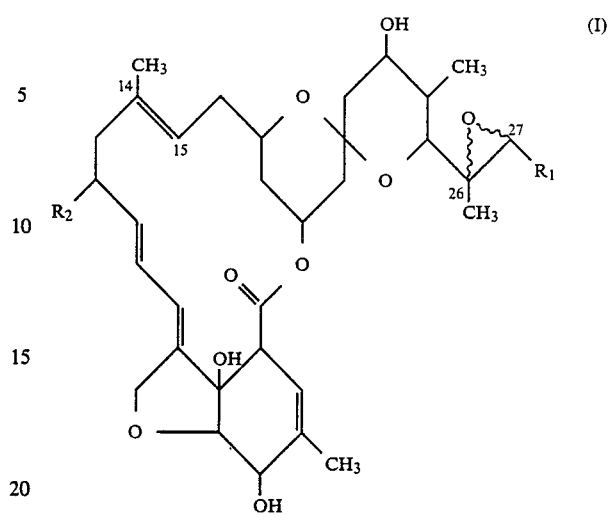

(I)

wherein $R_1$ is methyl or isopropyl; $R_2$ is hydrogen, methyl or ethyl; and an inert carrier; wherein said composition is used to control endo- or ectoparasites which infect warm blooded animals or to control acarids or insects which infest crops, trees, shrubs, stored grains and ornamentals.

* * * * *

UNITED STATES PATENT AND TRADEMARK OFFICE
CERTIFICATE OF CORRECTION

PATENT NO. : 4,876,272

DATED : October 24, 1989

INVENTOR(S) : Goro Asato; Susan Y. Tamura

It is certified that error appears in the above-identified patent and that said Letters Patent is hereby corrected as shown below:

TITLE PAGE:
In the title, "MONO- AND DIEPOXIDE" should be replaced with --MONOEPOXIDE--.

In col. 9, lines 57-58, claim 1, the portion of the lines reading "hydrogen, methyl or ethyl" should read --hydrogen or ethyl--; line 60, claim 2, the word "methyl" should be replaced with --hydrogen or ethyl--; line 64, claim 3, a comma should appear after the word orally; and lines 65-66, claim 3, the word "ectoparasited," should be replaced with --ectoparasites, a--.

In col. 10, lines 24-25, claim 3, the portion of the lines reading "hydrogen, methyl or ethyl" should read --hydrogen or ethyl--; line 27, claim 4, the word "methyl" should be replaced with --hydrogen or ethyl--; lines 58-59, claim 5, the portion of the lines reading "hydrogen, methyl or ethyl" should read --hydrogen or ethyl--; line 61, claim 6, the word "methyl" should be replaced with --hydrogen or ethyl--; and line 64, claim 7, the phrase "foliage plants" should read --foliage of plants--.

UNITED STATES PATENT AND TRADEMARK OFFICE
CERTIFICATE OF CORRECTION

PATENT NO.   : 4,876,272

DATED        : October 24, 1989

INVENTOR(S)  : Goro Asato; Susan Y. Tamura

It is certified that error appears in the above-identified patent and that said Letters Patent is hereby corrected as shown below:

In col. 11, lines 23-24, claim 7, the portion of the lines reading "hydrogen, methyl or ethyl" should read --hydrogen or ethyl--; and line 26, claim 8, the word "methyl" should be replaced with --hydrogen or ethyl--.

In col. 12, lines 23-24, claim 9, the portion of the lines reading "hydrogen, methyl or ethyl" should read --hydrogen or ethyl--.

Signed and Sealed this

Sixteenth Day of July, 1991

*Attest:*

HARRY F. MANBECK, JR.

*Attesting Officer*

*Commissioner of Patents and Trademarks*